United States Patent

Lorenz et al.

[11] 4,207,253
[45] Jun. 10, 1980

[54] METHOD OF MAKING COPOLYMERIZABLE, ULTRAVIOLET LIGHT ABSORBER (2-CYANO-3,3-DIPHENYLACRYLOXY) ALKYLENE ACRYLIC ACID ESTERS

[75] Inventors: Donald H. Lorenz, Basking Ridge; Bruce A. Gruber, Bloomingdale, both of N.J.

[73] Assignee: GAF Corporation, New York, N.Y.

[21] Appl. No.: 16,134

[22] Filed: Mar. 1, 1979

Related U.S. Application Data

[63] Continuation-in-part of Ser. No. 006,787, Jan. 26, 1979.

[51] Int. Cl.² ........................................... C07C 121/70
[52] U.S. Cl. ................................................. 260/465 D
[58] Field of Search ..................................... 260/465 D

[56] References Cited

U.S. PATENT DOCUMENTS

| | | | |
|---|---|---|---|
| 3,644,466 | 2/1972 | Strobel et al. | 260/465 D |
| 3,993,684 | 11/1976 | Dunnavant et al. | 260/465 D X |

*Primary Examiner*—Dolph H. Torrence
*Attorney, Agent, or Firm*—Walter C. Kehm; Walter Katz

[57] ABSTRACT

This invention relates to a method of making in high yield light absorber compounds which are (2-cyano-3,3-diphenylacryloxy) alkylene acrylic acid esters having the formula:

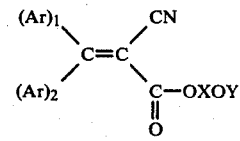

where
- $(Ar)_1$ and $(Ar)_2$ are aromatic carbocyclic nuclei of the benzene and naphthalene series and are independently selected from phenyl or phenyl substituted with alkyl, halo, alkoxy, carboxy, carbalkoxy, cyano, acetyl, benzoyl, phenyl, alkyl phenyl, phenoxy phenyl, alkyl substituted phenoxy, or alkoxy phenyl substituted phenyl, and naphthyl;
- X is alkylene, $C_2$-$C_{17}$, unsubstituted or substituted with halo, cyano, alkyl, alkoxy, alkoxyalkyl, or alkoxyalkyleneoxy, $C_1$-$C_6$; and
- Y is copolymerizable radical selected from acryloyl, alkylacryloyl, acryloxyalkyl, acryloxyhydroxyalkyl and alkylacryloxyhydroxyalkyl, $C_3$-$C_{12}$.

The method comprises:
(a) acylating a hydroxyalkylene cyanoacetate with an acylating agent to form an acylated intermediate whose hydroxy radical is protected by an acyl group which is convertible to hydroxy by hydrolysis,
(b) condensing the acyl intermediate with a benzophenone,
(c) hydrolyzing the condensed compound to form the corresponding condensed hydroxy compound; and,
(d) esterifying the hydroxy compound with an acryloyl halide or an acrylic acid to provide the desired product.

12 Claims, No Drawings

METHOD OF MAKING COPOLYMERIZABLE, ULTRAVIOLET LIGHT ABSORBER (2-CYANO-3,3-DIPHENYLACRYLOXY) ALKYLENE ACRYLIC ACID ESTERS

This is a continuation-in-part of application Ser. No. 006,787, filed Jan. 26, 1979.

BACKGROUND OF THE INVENTION

1. Field of the Invention

This invention relates to a method of making ultraviolet light absorber compounds and, more particularly, to a method of preparing 2-cyano-3,3-diphenylacryloxy acrylic acid ester compounds in high yield. The compounds herein copolymerize with vinyl monomers to produce polymer materials having improved resistance to degradation to light.

2. Description of the Prior Art

Various organic compounds exhibit the power to absorb electromagnetic radiation and can be incorporated in various plastic materials such as transparent sheets which act as filters for all the radiation passing through and will transmit only such radiations as are not absorbed by the sheet and/or the absorbing agent. Such filters find use in many technical and commercial applications.

Numerous cyano acrylic compounds have been suggested as absorbents for the range of radiations described above. For specific compounds, see U.S. Pat. Nos. 3,081,280; 3,272,810; 3,644,466; 3,256,312 and 3,215,724. These ultraviolet absorbers are mechanically mixed with the plastic materials to prevent discoloration and degradation of the material. However, it has been observed that such absorbers sometimes fail or are blocked out of the plastic under adverse weather conditions before the lifetime of the protected material. Also, it is not possible to use all of these ultraviolet absorbers with radiation curing of the plastic material. Another disadvantage of these ultraviolet absorbers is the high amount of absorber needed for protection of some materials.

RELATED PATENT APPLICATIONS

Copending patent application Ser. No. 006,787, filed Jan. 26, 1979, by the same applicants as herein, and assigned to the same assignee, describes novel copolymerizable ultraviolet light absorber compounds which are substantially free of the disadvantages of the prior art. This application is a continuation-in-part of said copending patent application.

SUMMARY OF THE INVENTION

What is provided herein is a method of making in high yield copolymerizable ultraviolet light absorber compounds which are (2-cyano-3,3-diphenylacryloxy) alkylene acrylic acid esters of the formula:

$$(Ar)_1 \diagdown \diagup CN$$
$$\phantom{xxxx} C=C$$
$$(Ar)_2 \diagup \diagdown \underset{\underset{O}{\|}}{C}-OXOY$$

where $(Ar)_1$ and $(Ar)_2$ are aromatic carbocyclic nuclei of the benzene and naphthalene series and are independently selected from phenyl or phenyl substituted with alkyl, halo, alkoxy, carboxy, carbalkoxy, cyano, acetyl, benzoyl, phenyl, alkyl phenyl, phenoxy phenyl, alkyl substituted phenoxy, or alkoxy phenyl substituted phenyl, and naphthyl;

X is alkylene, $C_2$–$C_{17}$, unsubstituted or substituted with halo, cyano, alkyl, alkoxy, alkoxyalkyl, or alkoxyalkyleneoxy, $C_1$–$C_6$; and, Y is copolymerizable radical selected from acryloyl, alkylacryloyl, acryloxyalkyl, acryloxyhydroxyalkyl and alkylacryloxyhydroxyalkyl, $C_3$–$C_{12}$.

The method comprises:

(a) acylating hydroxyalkylene cyanoacetate with an acylating agent to form an acylated intermediate whose hydroxy radical is protected by an acyl group which is convertible to hydroxy by hydrolysis.

(b) condensing the acyl intermediate with a benzophenone, (c) hydrolyzing the condensed compound to reform the corresponding hydroxy compound, and, (d) esterifying the condensed hydroxy compound with an acryloyl halide or an acrylic acid to provide the desired product.

DETAILED DESCRIPTION OF THE INVENTION

Suitable $(Ar)_1$ and $(Ar)_2$ groups are given in U.S. Pat. No. 3,644,466, including representative starting benzophenone compounds. In the best mode of the invention both $(Ar)_1$ and $(Ar)_2$ are phenyl.

The X groups are unsubstituted or substituted alkylene radicals, $C_2$–$C_{17}$. The preferred groups are unsubstituted lower alkylene, $C_2$–$C_6$, which are derived synthetically from ethylene glycol, propylene glycol, butanediol, and the like. The best mode is represented by —$CH_2$—$CH_2$—.

The Y radical is copolymerizable with vinyl monomers so that the ultraviolet absorber becomes an integral part of the polymer. Suitable Y groups are derived from acryloyl, alkylacryloyl, acryloxyalkyl, acryloxyhydroxyalkyl and alkylacryloxyhydroxyalkyl, $C_3$–$C_{12}$. The preferred groups are acryloyl, methacryloyl, glycidyl acryloyl and glycidyl methacryloxy. The best mode is represented by acryloyl or methacryloyl.

The compounds of the invention contain ultraviolet light absorber and copolymerizable portions in the same molecule. These portions are effectively separated by the X radical so that each can perform its own function without interference from the other. Therefore, the absorber portion does not inhibit the copolymerization, and the Y radical does not affect the light absorbing properties of the molecule.

In the method of the invention, the hydroxy group of the hydroxyalkyl cyanoacetate starting material first is protected by acylation to form an acyl group which is convertible by hydrolysis to the hydroxy compound. Acylation is carried out with acetic anhydride or acetyl chloride, usually, to provide the corresponding acetoxyalkyl cyanoacetate. The protected compound then is condensed with a benzophenone in a Knoevenagel reaction to provide the acetoxyalkyl (2-cyano-3,3-diphenyl) acrylate in excellent yield. Hydrolysis of the protecting acetyl group affords the corresponding hydroxyalkyl (2-cyano-3,3-diphenyl) acrylate intermediate, which is then directly esterified with a suitable acryloyl halide or acrylic acid to give the desired (2-cyano-3,3-diphenylacryloyloxy) alkylene acrylic acid ester compounds.

The method of the invention is particularly advantageous in that it affords the intermediate and product compounds in high yield. A feature of the process is the protection of the hydroxy group before carrying out the Knoevenagel reaction. This enables the Knoevenagel condensation to proceed in excellent yield to the desired intermediate, whereas previous condensations without protection gave very low yields. Then the protecting group is removed by hydrolysis under conditions which do not affect the remaining ester portion of the molecule. The final esterification reaction with the acryloyl halide or acrylic acid also is a high yield reaction, and thus the overall sequence of steps gives the desired acrylic acid ester compounds in excellent yields of above 30%.

The method of the invention is summarized in the flow sheet below where X and Y are as defined above, and Z is a halide or hydroxyl group.

Typical X groups are —$CH_2CH_2$, —$CH_2CH_2CH_2$—, —$CH_2CH_2CH_2CH_2$—, and the like.

Representative Y groups are

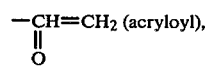

(acryloyl),

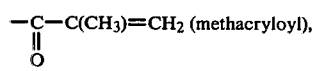

(methacryloyl),

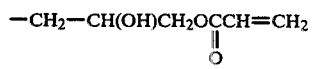

(3-acryloxy-2-hydroxypropyl), and

(3-methacryloxy-2-hydroxypropyl).

METHOD OF INVENTION

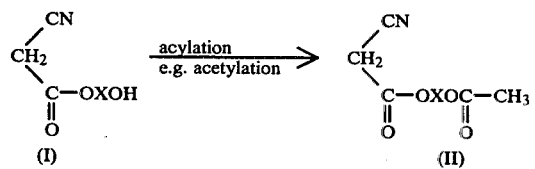

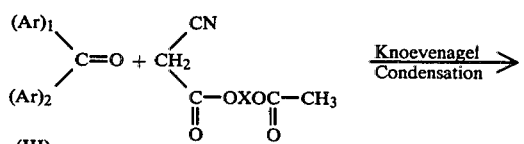

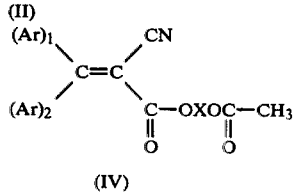

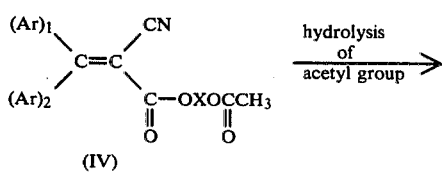

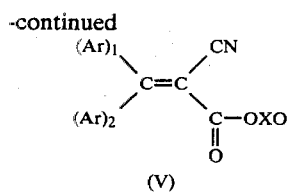

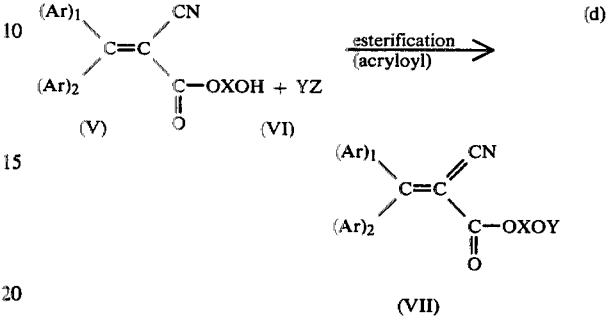

The hydroxyalkyl cyanoacetate starting material (I) for step (a) is prepared by reacting cyanoacetic acid with a lower dihydric alcohol as described in U.S. Pat. No. 3,644,466, Example 3, cols. 7–8.

In step (a), the hydroxy group of the hydroxyalkyl cyanoacetate (I) is protected by acylation, suitably by acetylation with acetic anhydride, to give the corresponding acetoxyalkyl cyanoacetate intermediate (II).

Step (b) in the process comprises a Knoevenagel condensation of a suitable benzophenone (III) with (II) to produce an acetoxyalkyl (2-cyano-3,3-diphenyl) acrylate (IV). The Knoevenagel reaction is generally run in the presence of a solvent, such as benzene, toluene, or ethylenedichloride, under reflux, usually at a temperature between 80° and 100° C. for about 24 hours. The reaction preferably proceeds in a nitrogen atmosphere and in the presence of glacial acetic acid and ammonium acetate as a catalyst. Conventional washings of the product with water and saturated bicarbonate solution are done prior to the drying, removing the solvent, and recovering the product.

The third step (c) in the synthesis is the removal only of the protecting acetyl ester group to provide the corresponding free hydroxyalkyl compound (V). This hydrolysis preferably is carried out under acid conditions in alcohol at reflux temperatures.

The final step (d) in the method of the invention involves esterification with a reactive acryloyl compound (VI), such as an acryloyl halide, e.g. acryloyl chloride or acryloyl bromide, or with an acrylic acid, to provide the desired (2-cyano-3,3-diphenylacryloyloxy) alkylene acrylic acid ester (VII). The reaction is carried out in an inert solvent, suitably an aromatic or aliphatic hydrocarbon or halogenated hydrocarbon, such as toluene, benzene, chloroform or ethylene dichloride, or in acetone, at a suitable temperature, generally ranging from room temperature to the reflux temperature of the solvent, e.g. if chloroform, at about 61° C., and in the presence of a base, such as sodium bicarbonate, to absorb the acid by-product of the reaction. Suitably the molar ratios of the reactants are controlled to provide at least a 1:1 molar ratio of the acryloyl halide to the hydroxyalkyl (2-cyano-3,3-diphenyl) acrylate. Preferably an excess of the acryloyl chloride is used. The reaction is run for about 1–5 hours at the reflux temperature.

When acrylic acid is used in place of an acryloyl chloride in step (d), water is distilled out of the reaction mixture as an azeotrope with the solvent. Preferably, a polymerization inhibitor, such as phenothiazine or methoxyphenol, is included in the reaction mixture, in an amount of about 200–1000 ppm, to prevent polymerization of the acrylic acid reactant. The reaction with acrylic acid generally is run at a somewhat higher temperature than with the acryloyl chloride, usually at about 80°–110° C., for about 10 to about 20 hours.

The overall yield of the process to give product (VII) is about 30%.

The compounds (VII) prepared by the method of the invention are copolymerized, for example, with a urethane oligomer, by radiation curing, to provide useful polymeric coatings.

The following examples will describe the invention with more particularity.

EXAMPLE 1

2-(2-Cyano-3,3-Diphenylacryloxy) Ethyl Acrylate

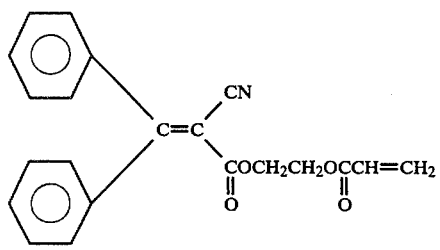

(a) 2-Acetoxyethyl 2-Cyanoacetate

Cyanoacetylic acid was esterified with ethylene glycol according to U.S. Pat. No. 3,644,466 (Col. 7–8, Ex. 3) to give the 2-hydroxyethyl 2-cyanoacetate starting material in 74% yield.

Into a 1 l. three-neck round bottom flask with magnetic stirrer, dropping funnel, thermometer, and drying tube was charged 122 g. (1.2 moles) of acetic anhydride and 10 drops of concentrated sulfuric acid. Then 129 g. (1 mole) of 2-hydroxyethyl cyanoacetate was added dropwise with stirring while maintaining the reaction temperature below 75° C. The acylated ester thus produced was then diluted with 100 ml. of water and the excess acid was neutralized with solid potassium carbonate. The oil layer was separated and dried to yield 130 g. (79%) of the desired compound.

(b) 2-Acetoxyethyl 2-Cyano-3,3-Diphenylacrylate

A 1 l. three-neck round bottom flask fitted with a mechanical stirrer, a thermometer and a Dean-Stark trap fitted with a reflux condenser was charged with 200 ml. of toluene, 182 g. (1 mole) of benzophenone, 205 g. (1.2 moles) of 2-acetoxyethyl 2-cyanoacetate, 40 ml. of glacial acetic acid, 16 g. of ammonium acetate. The contents were heated to reflux (110° C.) for 24 hours while the theoretical amount of water by-product was removed by azeotropic distillation. Upon removal of the solvent, as well as unreacted starting material by vacuum distillation, a yield of 200 g. (60%) of the desired product was obtained.

(c) 2-Hydroxyethyl 2-Cyano-3,3-Diphenylacrylate

A charge of 800 ml. of methanol, 335 g. (1 mole) of 2-acetoxyethyl 2-cyano-3,3-diphenylacrylate and 10 drops of concentrated hydrochloric acid was heated at 65° C. for 18 hours. Evaporation of the solvent left 235 g. (80%) of the intermediate compound as an amber, viscous oil.

(d) 2-(2-Cyano-3,3-Diphenylacrylate) Ethyl Acrylate

To a charge of 3 l. of methylene chloride, 179 g. of potassium carbonate and 293 g. (1 mole) of 2-hydroxyethyl 2-cyano-3,3-diphenylacrylate was added 118 g. (1.3 moles) of acryloyl chloride and the contents were heated at 41° C. for 2 hours. The reaction mixture then was diluted with 3 l. of water and neutralized with solid potassium carbonate. The organic layer was separated, dried and evaporated, leaving 274 g. (79%) of an amber oil, which was characterized by NMR as the product compound.

EXAMPLE 2

The compound of Example 1 was prepared using acrylic acid instead of acryloyl chloride in Step (d) of Example 1 as follows:

(d) A charge of 347 g. (1 mole) of 2-hydroxyethyl 2-cyano-3,3-diphenylacrylate in 1.5 l. of toluene was heated at reflux (110° C.) to remove residual water and the solution was cooled to 30° C. Then 96 g. (1.3 moles) of acrylic acid, 5 g. of p-toluene sulfonic acid and 350 mg. of phenothiazine was added and the solution was heated at reflux for 16 hours. The reaction mixture then was cooled to room temperature and 1 l. of water was added and the solution was neutralized with solid potassium carbonate. The organic layer then was dried and evaporated to yield 328 g. (80% yield, about 75% purity) of an amber oil of the product compound.

EXAMPLE 3

2-(2-Cyano-3,3-Diphenylacryloxy) Ethyl Methacrylate

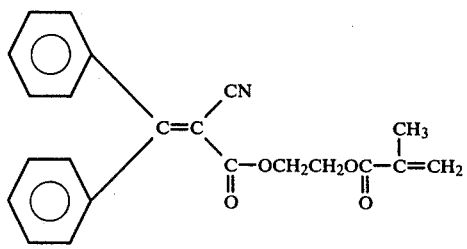

Using an equivalent amount of methacryloyl chloride in place of acryloyl chloride in Step (d) of Example 1, the desired ethyl methacrylate compound is obtained in comparable yield.

EXAMPLE 4

3-(2-Cyano-3,3-Diphenylacryloyl) Propyl Methacrylate

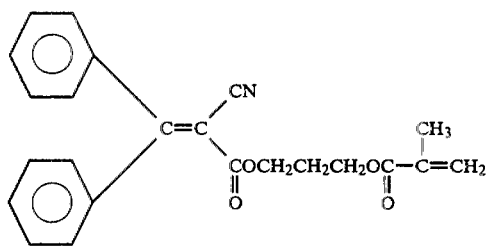

Using an equivalent amount of propylene glycol in place of ethylene glycol in Example 3, there is produced the desired propylmethacrylate compound in comparable yield.

EXAMPLE 5

4-(2-Cyano-3,3-Diphenylacryloyl) Butyl Acrylate

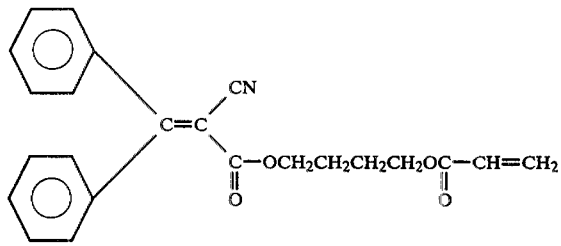

By substituting 1,4-butanediol in place of ethylene glycol in Example 1, there is produced the corresponding butyl acrylate.

EXAMPLE 6

2-Hydroxy-3- 2-(2-Cyano-3,3-Diphenyl) Ethoxy Propyl Acrylate

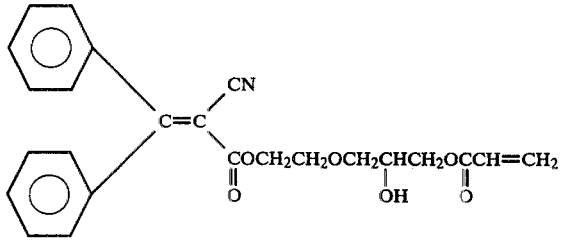

The procedure of Example 1 is followed except for (d) as follows:

Into a round bottom flask is charged 29.3 g. (0.1 mole) of 2-hydroxyethyl 2-cyano-3,3-diphenylacrylate, 21.3 g. (0.15 mole) glycidyl acrylate and 0.27 g. (0.0025 mole) tetramethylammonium chloride. The mixture was heated at 70°–90° for 5 hours. Thereafter excess glycidyl acrylate was removed by vacuum distillation. The remaining amber oil was the desired ethoxy propyl acrylate product.

EXAMPLE 7

2-Hydroxy-3-[2-(2-Cyano-3,3-Diphenylacryloxy) Ethoxy] Propyl Methacrylate

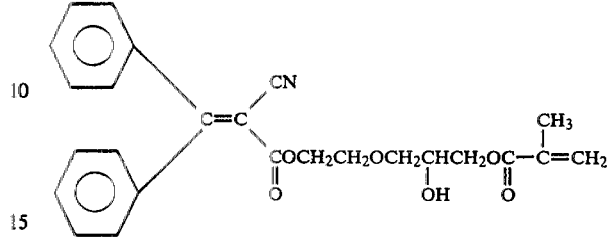

Using glycidyl methacrylate in place of glycidyl acrylate in Example 6 gives the corresponding methacrylate compound.

While certain preferred embodiments of the present invention have been illustrated by way of specific example it is to be understood that the present in no way to be deemed as limited thereto but should be construed as broadly as all for any equivalents thereof.

What is claimed is:

1. A method of making copolymerizable ultraviolet light absorber (2-cyano-3,3-diphenylacryloxy) alkylene acrylic acid esters in high yield having the formula:

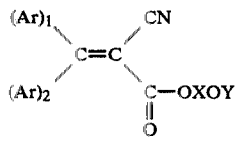

where
- $(Ar)_1$ and $(Ar)_2$ are aromatic carbocyclic nuclei of the benzene and naphthalene series and are independently selected from phenyl or phenyl substituted with alkyl, halo, alkoxy, carboxy, carbalkoxy, cyano, acetyl, benzoyl, phenyl, alkyl phenyl, phenoxy phenyl, alkyl substituted phenoxy, or alkoxy phenyl substituted phenyl, and naphthyl;
- X is alkylene, $C_2$–$C_{17}$, unsubstituted or substituted with halo, cyano, alkyl, alkoxy, alkoxyalkyl, or alkoxyalkyleneoxy, $C_1$–$C_6$; and,
- Y is copolymerizable radical selected from acryloyl, alkylacryoyl, acryloxyalkyl, acryloxyhydroxyalkyl and alkylacryloxyhydroxyalkyl, $C_3$–$C_{12}$, which comprises the steps of:

(a) acylating a hydroxyalkylene cyanoacetate having the formula:

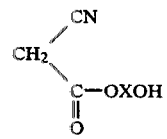

where X is as defined above, with an acetyl acylating agent capable of reacting with the hydroxy group to form an acetyl acylated intermediate which is convertible to hydroxy by hydrolysis, (b) condensing the acetyl acylated intermediate with a benzophenone having the formula:

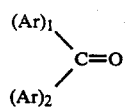

where $(Ar)_1$ and $(Ar)_2$ are as defined above, to form a condensed intermediate which is

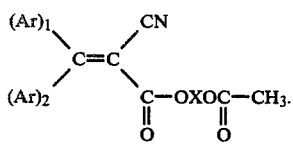

(c) hydrolyzing the condensed intermediate to form the corresponding condensed hydroxy compound which is

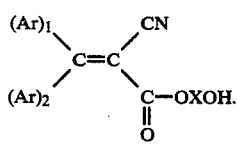

and;

(d) esterifying the condensed hydroxy compound with an acryloyl halide or acrylic acid having the formula:

YZ where Y is as defined above and Z is a halide or hydroxyl group, to form said desired compounds.

2. A method according to claim 1 in which both $(Ar)_1$ and $(Ar)_2$ are phenyl.

3. A method according to claim 1 in which X is alkylene, $C_2-C_6$.

4. A method according to claim 1 in which Y is acryloyl, methacryloyl, 3-acryloxy-2-hydroxypropyl or 3-methacryloxy-2-hydroxypropyl.

5. A method according to claim 1 in which both $(Ar)_1$ and $(Ar)_2$ are phenyl, X is alkylene, $C_2-C_6$ and Y is acryloyl, methacryloyl, 3-acryoxy-2-hydroxypropyl or 3-methacryloxy-2-hydroxypropyl.

6. A method according to claim 1 in which in step (c) the hydrolysis is carried out under acid conditions in alcohol.

7. A method according to claim 1 in which in step (d), YZ is an acryloyl halide.

8. A method according to claim 1 in which in step (d), YZ is an acrylic acid.

9. A method according to claim 1 in which in step (d) an excess of the acryloyl halide or acrylic acid over a 1:1 molar ratio of reactants is used.

10. A method according to claim 1 in which step (d) is carried out with an acryloyl chloride or acryloyl bromide in a solvent in the presence of a base.

11. A method according to claim 1 in which step (d) is carried out with an acrylic acid in an inert solvent which forms an azeotrope with the water by-product of the reaction which can be removed by distillation, and in the presence of a polymerization inhibitor to prevent polymerization of the acrylic acid reactant.

12. A method of making intermediates in the manufacture of copolymerizable ultraviolet light absorber (2-cyano-3,3-diphenylacryloxy) alkylene acrylic acid esters, said intermediates having the formula:

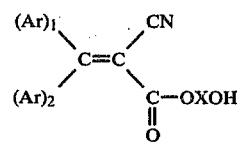

where
- $(Ar)_1$ and $(Ar)_2$ are aromatic carbocyclic nuclei of the benzene and naphthalene series and are independently selected from phenyl or phenyl substituted with alkyl, halo, alkoxy, carboxy, carbalkoxy, cyano, acetyl, benzoyl, phenyl, alkyl phenyl, phenoxy phenyl, alkyl substituted phenoxy, or alkoxy phenyl substituted phenyl, and naphthyl; and
- X is alkylene, $C_2-C_{17}$, unsubstituted or substituted with halo, cyano, alkyl, alkoxy, alkoxyalkyl, or alkoxyalkyleneoxy, $C_1-C_6$; which comprises the steps of:

(a) acetylating a hydroxyalkylene cyanoacetate having the formula:

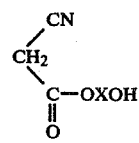

where X is as defined above, with an acetylating agent capable of reacting with the hydroxy group to form an acetyl compound which is convertible to hydroxy by hydrolysis, (b) condensing the acetyl compound with a benzophenone having the formula:

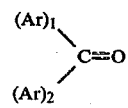

where $(Ar)_1$ and $(Ar)_2$ are as defined above, to form a condensed compound which is

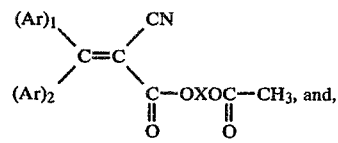

(c) hydrolyzing the condensed compound to form the desired intermediate.

* * * * *